(12) United States Patent
Yusa et al.

(10) Patent No.: US 8,506,992 B2
(45) Date of Patent: Aug. 13, 2013

(54) PERCUTANEOUS ABSORPTION-TYPE PHARMACEUTICAL PREPARATIONS

(75) Inventors: Yoshimi Yusa, Ibaraki (JP); Keiji Yamamoto, Ibaraki (JP); Tooru Kawashima, Ibaraki (JP)

(73) Assignee: Nitto Denko Corporation, Osaka (JP)

(*) Notice: Subject to any disclaimer, the term of this patent is extended or adjusted under 35 U.S.C. 154(b) by 1103 days.

(21) Appl. No.: 11/514,891

(22) Filed: Sep. 5, 2006

(65) Prior Publication Data

US 2007/0053967 A1 Mar. 8, 2007

(30) Foreign Application Priority Data

Sep. 5, 2005 (JP) ................. P.2005-256277

(51) Int. Cl.
*A61K 9/70* (2006.01)
*A61K 31/135* (2006.01)
*A61K 47/30* (2006.01)
*A61K 47/32* (2006.01)

(52) U.S. Cl.
USPC ...... 424/449; 514/649; 514/772.3; 514/772.6

(58) Field of Classification Search
USPC ............... 424/449; 514/649, 772.3, 772.6
See application file for complete search history.

(56) References Cited

U.S. PATENT DOCUMENTS

| 5,374,429 A | * | 12/1994 | Kinoshita et al. | ............. 424/448 |
| RE36,420 E | | 11/1999 | Nakano et al. | |
| 6,306,492 B1 | * | 10/2001 | Yamada et al. | ............. 428/317.7 |

FOREIGN PATENT DOCUMENTS

| AU | 707 661 B2 | 5/1997 |
| EP | 1352649 A2 | 10/2003 |
| JP | 5-309772 A | 11/1993 |
| JP | 6-30983 A | 2/1994 |
| JP | 9255563 A | 9/1997 |
| JP | 10-67652 A | 3/1998 |
| JP | 10-287557 A | 10/1998 |
| JP | 2003-116908 A | 4/2003 |
| JP | 2003-277255 A | 10/2003 |
| JP | 2004-131383 A | 4/2004 |

OTHER PUBLICATIONS

The Polymer Handbook, 1989, ed. J. Brandrup and E.H. Immergut, pp. 210-212 and 233-238.*
Extended European Search Report dated Apr. 2, 2009.
Decision on Rejection issued May 25, 2011, in counterpart Chinese Application No. 200610128124.3.
Office Action dated Oct. 15, 2012, issued by the Korean Intellectual Property Office in counterpart Korean Patent Application No. 10-2006-84782.
Office Action dated Nov. 30, 2011, issued by the Canadian Intellectual Property Office in corresponding Canadian Patent Application No. 2,558,432.
Japanese Office Action issued on Jan. 5, 2011 in the corresponding Japanese Patent Application No. 2005-256277.

* cited by examiner

*Primary Examiner* — Abigail Fisher
(74) *Attorney, Agent, or Firm* — Sughrue Mion, PLLC

(57) ABSTRACT

A percutaneous absorption-type pharmaceutical preparation containing a sublimation drug is provided, where from a plaster layer, a drug is released as volatile substance with a lapse of time, but the released drug has no adverse effect on the handling of the preparation, and the quality of the preparation is maintained in storage over a long period of time. A percutaneous absorption-type pharmaceutical preparation, which comprises: a support comprising a plastic film and a nonwoven fabric; and a plaster layer containing a sublimation drug, wherein the plastic film and the nonwoven fabric are laminated with an adhesive having a glass transition temperature of 10° C. or higher, and the plaster layer is laminated on opposite side of the plastic film surface that the nonwoven fabric is laminated with.

4 Claims, 2 Drawing Sheets

PERCUTANEOUS ABSORPTION-TYPE PHARMACEUTICAL PREPARATIONS

FIELD OF THE INVENTION

The present invention relates to a percutaneous absorption-type pharmaceutical preparation applied to the skin surface for administering a drug to the living body through the skin. More particularly, the invention relates to a percutaneous absorption-type pharmaceutical preparation containing a sublimation drug on a plaster layer, from which the drug is released as volatile substance with a lapse of time, but the released drug has no adverse effect on the handling of the preparation and the quality of the preparation is maintained in storage over a long period of time.

BACKGROUND OF THE INVENTION

In recent years, percutaneous absorption-type pharmaceutical preparations have actively been developed as a means of administering a drug through the surface of skin into the living body for the purpose of prolongation of the expression of pharmacological effects or reduction of the side effect. In particular, an adhesive plaster has attracted a great deal of attention in easiness of handling and the strict dose.

In such an adhesive plaster, a variety of ideas have been attempted to the drug-containing layers, and improvement of its transdermal property or immediate action as well as prolongation of the action have been studied from several view points.

As for the support of adhesive plasters, because they have to be applied to the skin surface, easiness of handling at the application, mobility (flexibility) responding to movement of the skin surface, no irritation to the skin, and so on, are required as important characters. In addition, it is also required to prevent reduction of the drug content due to shift of the drug to the support. In order to respond to such requirement, a laminated film prepared by gluing a plastic film onto a porous material via an adhesive (Patent Document 1: JP-A-5-309772), and a percutaneous absorption-type pharmaceutical preparation which is prepared by laminating a plaster layer on the surface of polyester film as support prepared by laminating a soft auto-foam onto a polyester film, have been proposed (Patent Document 2: JP-A-6-30983).

The so far proposed percutaneous absorption-type pharmaceutical preparations, however, have a problem that a sublimation drug contained in the plaster layer is released as volatile substance from the edge portion of the preparation with a lapse of time. The released drug is adsorbed in the adhesives contained in a support layer to cause plasticization of the adhesives, thereby decreasing the laminate strength between plastic films such as porous materials; thus, when the preparation is applied to or peeled off from the skin surface, in some cases a nonwoven fabric only is peeled off, leaving the plaster layer on the skin surface. In addition, the content of the drug to be contained in the plaster decreases due to release of the drug. Therefore, in a case of a sublimation drug being contained, a percutaneous absorption-type pharmaceutical preparation which is not accompanied by the above-mentioned problems has been desired.

SUMMARY OF THE INVENTION

In view of the above-mentioned circumstances, the problems to be solved by the invention is to provide a percutaneous absorption-type pharmaceutical preparation containing a sublimation drug on a plaster layer, from which the drug is released as volatile substance with a lapse of time, but the released drug has no adverse effect on the handling of the preparation and the quality of the preparation is maintained in storage over a long period of time.

The present inventors worked assiduously to solve the above problem, and found that the use of an adhesive of which the glass transition temperature is higher than a certain value decreases adsorption of the released drug to the adhesive, suppresses decrease of the laminate strength between a porous material such as nonwoven fabric and a plastic film, and further suppresses decrease of the content of the drug contained in the plaster. Thus, the invention was completed.

Accordingly, the invention is as follows.

(1) A percutaneous absorption-type pharmaceutical preparation, which comprises: a support comprising a plastic film and a nonwoven fabric; and a plaster layer containing a sublimation drug, wherein the plastic film and the nonwoven fabric are laminated with an adhesive having a glass transition temperature of 10° C. or higher, and the plaster layer is laminated on opposite side of the plastic film surface that the nonwoven fabric is laminated with.

(2) The percutaneous absorption-type pharmaceutical preparation as described in the item (1), wherein the adhesive is one selected from the group consisting of polyester resin, polyester urethane resin, polyvinyl acetate resin, ethylene-vinyl acetate resin, polyacrylate resin, and vinyl chloride-vinyl acetate copolymer resin.

(3) The percutaneous absorption-type pharmaceutical preparation as described in the item (1) or (2), wherein the plastic film and the nonwoven fabric both are made from polyester.

(4) The percutaneous absorption-type pharmaceutical preparation as described in any one of the items (1) to (3), wherein the plaster layer contains the sublimation drug in an amount of 1-40% by weight.

(5) The percutaneous absorption-type pharmaceutical preparation as described in any one of the items (1) to (4), wherein the sublimation drug is tulobuterol.

In the percutaneous absorption-type pharmaceutical preparation of the invention, the time-depending decrease of the laminate strength between a nonwoven fabric and a plastic film and of the content of a sublimation drug can be prevented by using a support in which the plastic film is laminated on the nonwoven fabric through an adhesive having a high glass transition temperature. Therefore, according to the invention, a percutaneous absorption-type pharmaceutical preparation containing a sublimation drug can be provided, in that when the preparation is applied to or peeled off from the skin surface, the nonwoven fabric is not peeled off from the plastic film layer, and the quality of the preparation is stably maintained in a long-term storage.

EXPLANATION OF LETTERS OR NUMERALS

1. Polyester nonwoven fabric
2. Adhesive layer
3. Polyester film
4. Plaster layer

DETAILED DESCRIPTION OF THE INVENTION

The invention will be explained in detail as follow.

Figure 1:
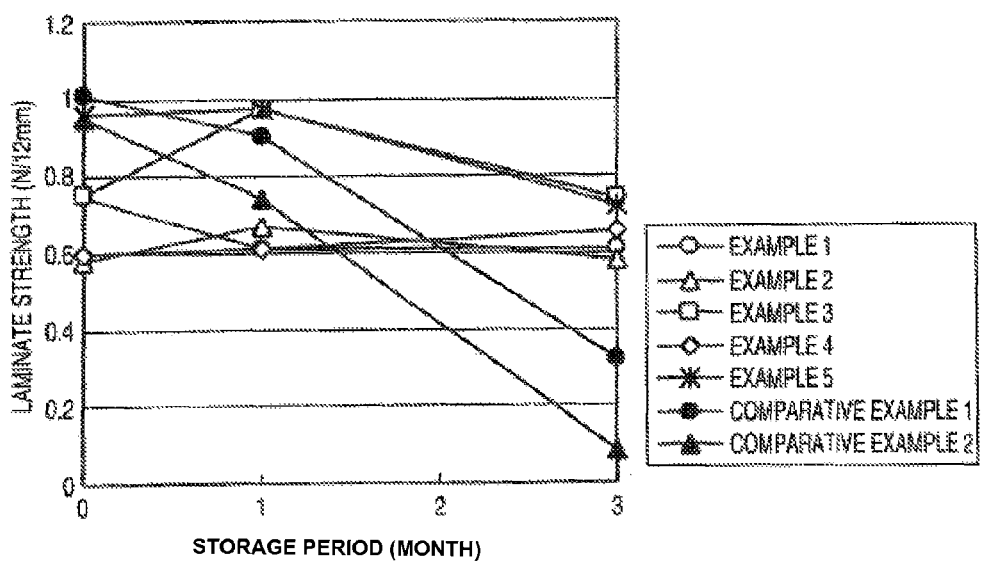
FIG. 1 shows a graph showing the change over time of the laminate strength of the pharmaceutical preparation in Experiment 1.
Figure 2:
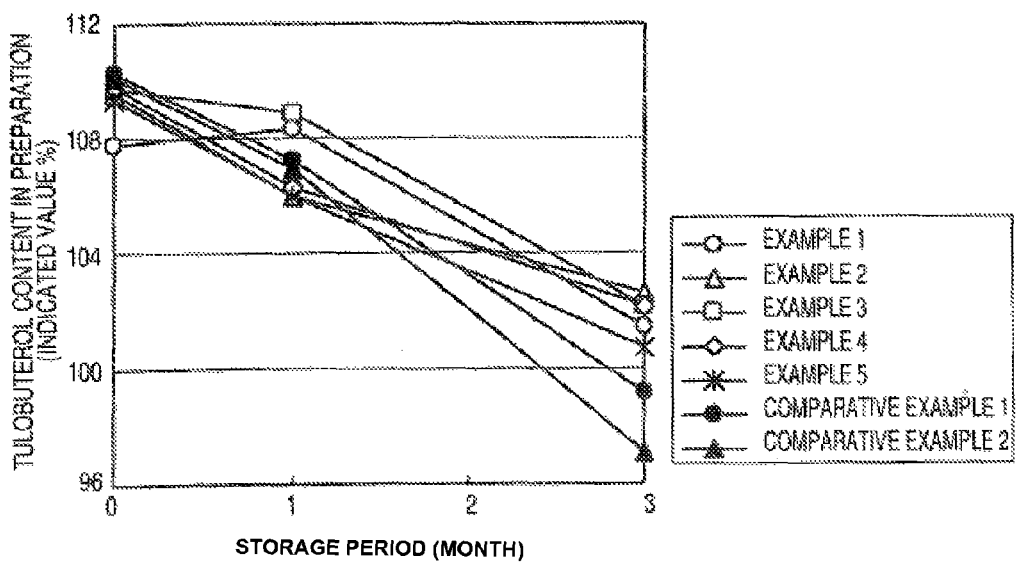
FIG. 2 shows a graph showing the change over time of the drug content in the plaster layer in Experiment 2.
Figure 3:
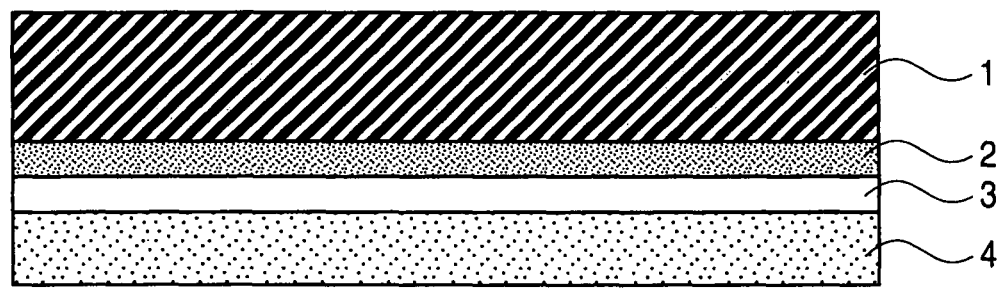
FIG. 3 shows a cross section view of the percutaneous absorption-type pharmaceutical preparation of the invention.

As shown in FIG. 3, the invention provides a percutaneous absorption-type pharmaceutical preparation which comprises a support comprising a plastic film 3, on which a nonwoven fabric 1 is laminated with an adhesive 2, and a plaster layer 4 containing a drug, which is laminated on opposite side of the plastic film surface that is laminated with the nonwoven fabric.

The support in the percutaneous absorption-type pharmaceutical preparation of the invention comprises a plastic film on which a nonwoven fabric is laminated with an adhesive.

The plastic film includes non-porous film or sheet formed with polyethylene, polypropylene, polyester, polyvinyl acetate, polyurethane, polyvinyl alcohol, vinylidene polychoride, polyamide, polyethylene-vinyl acetate, and the like.

The nonwoven fabric has the basic weight in the range of 5-20 g/m$^2$, and its raw material comprises 1 or more species of natural fiber such as cotton, synthetic fiber such as polyester, nylon, vinylon, rayon, acetate, and the like.

Among these plastic film and nonwoven fabric, polyester is preferred for all of the support, in view of non-permeation of drugs.

As the polyesters for use in polyester films or polyester nonwoven fabrics, those including polyethylene terephthalate as major component are preferred considering safety (non-toxic) to the living body, practical use, and wide use. Specifically, ethylene terephthalate homopolymer, co-polymer containing ethylene terephthalate as a major unit and other ester unit, a mixture of ethylene terephthalate homopolymer and polymer comprising other ester unit, and the like may be used.

The other ester unit for use in copolymerization or mixing includes, for example, as dicarboxylic acid component, aromatic dicarboxylic acid such as isophthalic acid, diphenyldicarboxylic acid, diphenyl ether dicarboxylic acid, diphenylsulfone dicarboxylic acid, naphthalenedicarboxylic acid, and the like, and aliphatic dicarboxylic acid such as adipic acid, sebacic acid, and the like. As diol component, alkylene glycols such as trimethylene glycol, tetramethylene glycol, hexamethylene glycol, and the like, aromatic diols such as hydroquinone, resorcinol, bisphenol A, and the like, aliphatic diols such as bis(hydroxyethoxyphenyl)sulfone, bis(hydroxyethoxyphenyl)propane, and the like, and diethylene glycol, may be used.

The thickness of the plastic film is in approximately 0.5-10 μm, preferably 0.5-6 μm. In order to reduce irritation to the skin surface by the edge of support, the thickness is preferably made as thin as possible, and thus it is preferred to use a very thin film of 2-6 μm practically. When the thickness is less than 0.5 μm, it becomes practically difficult to obtain a support laminated with nonwoven fabric, and over 10 μm in thickness, for example, in a case of using polyester as a film material, rigidity possibly occurs to give coarse and stiff feeling (feeling of wrongness) when applied to the skin.

The basic weight of nonwoven fabric is approximately 5-20 g/m$^2$, preferably 8-20 g/m$^2$. When the basic weight is less than 5 g/m$^2$, it is possibly difficult to give a sufficient action and effect as nonwoven fabric in lamination to film, and the basic weight over 20 g/m$^2$ possibly affords coarse and stiff feeling to nonwoven fabric.

When a polyester nonwoven fabric is used, it is preferable to use the fabric in a smaller basic weight than that usually used, in order to remove coarse and stiff feeling after application to the skin surface.

In the support of the invention, the adhesive for use in lamination of nonwoven fabric on a plastic film includes, for example, those containing as a base resin such as polyester resin, polyester urethane resin, polyvinyl acetate resin, ethylene-vinyl acetate resin, polyacrylate resin, vinyl chloride-vinyl acetate copolymer resin, or the like, of which the glass transition temperature (hereinafter, sometimes referred to as Tg) is 10° C. or higher. Preferably, those in the range of 10° C.-90° C., more preferably 40° C.-90° C., may be used. At Tg less than 10° C., the adhesive easily adsorbs an released drug, resulting in striking plasticization, unfavorably. At Tg over 90° C., the adhesive sometimes becomes too rigid. Therefore, it sometimes affects unfavorably on easiness of handling at the application or mobility (flexibility) responding to movement of the skin surface.

The resin composing the above adhesive includes preferably polyester resin and polyester urethane resin; the polyester resin includes, for example, amorphous polyester resin such as Vylon GK64CS (Toyobo Co., Ltd., hereinafter the same), Vylon 20SS, Vylon GK880, Vylon 885, Vylon 290, Vylon 295, Vylon 280, Vylon 270, Vylon 226, Vylon 245, Vylon 240, Vylon GK250, Vylon GK360, Vylon 660, Vylon 220, Vylon GK110, Vylon 103, Vylon 600, Vylon GK810, and the like. The polyester urethane resin includes Vylon UR-1400, Vylon UR-8200, Vylon UR-4125, Vylon UR-1350, and the like.

The support of the invention may be prepared, for example, by applying the above-mentioned adhesive alone or as a major solution dissolved in an organic solvent containing a crosslinking agent with a gravure coater at a rate of about 1-8 g/m$^2$, and then applying a nonwoven fabric under pressure, if required under heating. The crosslinking agent to be added to the major solution is exemplified by polyisocyanate compound. As an organic solvent, for example, methyl ethyl ketone, toluene, cyclohexane, and the like are included. These organic solvents may be used alone or in combination of two or more species. The use of such an adhesive suppresses adsorption of a drug (released as volatile substance from the plaster layer) to the adhesive on the support and prevents plasticization.

Alternatively, the adhesion of a nonwoven fabric onto a film may be achieved with a thermally fused adhesive to yield a support of the invention.

The thickness of the support is in the range of 5-500 μm, preferably 5-200 μm. In order to improve the adhesion and anchorage character with a plaster layer, the surface of plastic film on which a plaster layer is laminated is preferably treated by corona discharge, plasma or oxidation.

In the percutaneous absorption-type pharmaceutical preparation of the invention, a plaster layer in the above support is laminated on the opposite side of the plastic film laminated with the nonwoven fabric. The laminated plaster layer preferably contains an adhesive and a sublimation drug. It is desired that the exposed surface of the plaster layer is covered and protected with a mold-releasing liner such as paper or plastic film which has been subjected to peeling-off treatment by applying silicone resin or fluororesin, immediately before application to the skin.

As the adhesive contained in the plaster layer, acryl-type adhesive, natural rubber-type adhesive, synthetic rubber-type adhesive, acryl-type adhesive, vinyl ether-type adhesive, silicone-type adhesive, and the like may be used as far as they are effective in attaining the purpose of the invention. As the silicone-type adhesive, silicone rubber, dimethylsiloxane base, diphenylsiloxane base, and the like may be used. As the vinyl ether-type resin, polyvinyl methyl ether, polyvinyl ethyl ether, polyvinyl isobutyl ether, and the like are included.

Among these adhesives, acryl-type adhesive and rubber-type adhesive are preferably used in view of adhesiveness to the skin.

The above acryl-type adhesive comprises acryl-type polymer, and includes single polymers of alkyl(meth)acrylate or their copolymer.

In this connection, the alkyl in alkyl(meth)acrylate is preferably a straight or branched chain alkyl of 4-12 carbon atoms, and such an alkyl(meth)acrylate specifically includes butyl(meth)acrylate, t-butyl(meth)acrylate, pentyl(meth)acrylate, hexyl(meth)acrylate, heptyl(meth)acrylate, octyl(meth)acrylate, isooctyl(meth)acrylate, nonyl(meth)acrylate, isononyl(meth)acrylate, decyl(meth)acrylate, undecyl(meth)acrylate, dodecyl(meth)acrylate, 2-ethylhexyl(meth)acrylate, and the like. The alkyl(meth)acrylate is polymerized in the acryl-type adhesive, preferably at a rate of 50% by weight or more, more preferably at a rate of 60% by weight.

As an acryl-type polymer used in the invention, a copolymer of the above alkyl(meth)acrylate with one or more of monomer as mentioned below may also preferably be used.

The monomer includes functional monomers having at least one unsaturated double bond in the molecule and having a functional group such as a carboxyl group, hydroxyl group, sulfonic acid group, amino group, amido group, alkoxy group, cyano group or acyloxy group on the side chain [for example, an alkoxy-denatured monomer of alkyl(meth)acrylate derived by denaturation of the alkyl group of alkyl(meth)acrylate with a straight or branched chain alkoxy group of 1 to 4 carbon atoms (for example, methoxy, ethoxy, etc.) (specifically including 2-methoxyethyl(meth)acrylate, 2-ethoxyethyl(meth)acrylate), acrylonitrile, vinyl acetate, vinyl propionate, vinylpyrrolidone, vinylcaprolactam, (meth)acrylic acid, 2-hydroxyethyl(meth)acrylate, styrenesulfonic acid, (meth)acrylamide, 2-aminoethyl(meth)acrylate, and the like].

When a copolymer derived from an alkyl(meth)acrylate and the above functional monomer is used as the acryl-type copolymer, the alkyl(meth)acrylate may be used in an amount of 60-98% by weight, preferably 65-97% by weight, and the above monomer in an amount of 2-40% by weight, preferably 30-35% by weight, for copolymerization.

The rubber-type adhesive includes, for example, those comprising polyisobutyrene-polybutene type, styrene-diene-styrene block copolymer, styrene-butadiene type, nitrile type, chloroprene type, vinylpyridine type, polyisobutyrene type, butyl type, isoprene-isobutyrene type, and the like.

In particular, polyisobutyrene, styrene-diene-styrene block copolymer [for example, styrene-butadiene-styrene block copolymer (SBS), styrene-isoprene-styrene block copolymer (SIS), and the like are preferably used, in view of the solubility to drugs and adhesiveness to the skin. These may be used as a mixture.

The rubber type adhesive, in order to obtain a proper adhesiveness and drug solubility, may be used as a mixture of the same components or different components of which the viscosity average molecular weight is different. For example, in a case of polyisobutyrene, a mixture of high molecular weight polyisobutyrene of the viscosity average molecular weight of 300,000-2,500,000 and a medium molecular weight polyisobutyrene of the viscosity average molecular weight of 10,000-200,000 and/or a low molecular weight polyisobutyrene of the viscosity average molecular weight of 500-4,000, is preferred. In this connection, it is appropriate to blend a high molecular weight polyisobutyrene in a rate of 10-80% by weight, preferably 20-50% by weight, a medium molecular weight polyisobutyrene in 0-90% by weight, preferably 10-80% by weight, and a low molecular weight polyisobutyrene in 0-80% by weight, preferably 10-60% by weight. In this invention, the average molecular weight means the viscosity average molecular weight calculated from the Flory's viscosity formula.

The drug contained in the plaster layer in the invention is a sublimation drug which has a subliming property and of which the melting point is 40° C. or higher (solid at usual temperature). Such a drug includes those which is absorbed transdermally to exhibit a pharmacological effect, including locally or systemically active drugs, specifically, asthma relaxatives (tulobuterol), corticosteroids, analgesic anti-inflammatory agents, hypnotic sedatives, tranquilizers, antihypertensive agents, anti-hypertensive diuretics, antibiotics, anesthetics, antimicrobials, antifungal drugs, vitamins, coronary vasodilators, anti-histamine drugs, antitussives, sex hormones, anti-depressants, cerebral circulatory improving agents, antiemetics, anti-tumor agents, vital drugs, and the like. These drugs if required may be contained in combination of two or more species.

The content of these drugs in the plaster layer can be properly determined according to the kind of drug and the purpose of administration, and usually it is 1-40% by weight, preferably 2-30% by weight. When the content is less than 1% by weight, release of the therapeutically effective amount of the drug cannot be expected; and when the content is over 40% by weight, the therapeutic effect is restricted because of efficiency of absorption, and it is economically disadvantage.

The plaster layer in the invention is composed of a drug and an adhesive as major components, in which thermally plasticizing resin may be contained. Particularly, when a polyisobutyrene adhesive is used, it is desirous to add a thermally plasticizing resin.

The thermally plasticizing resin contained in the plaster layer together with a polyisobutyrene adhesive works as a proper diffusion disturbance during diffusion and migration of the drug in the plaster layer and releases continuously and efficiently the drug to the skin; thus, the drug is transdermally absorbed into the living body over a long period of time, resulting in prolongation of the drug efficacy. Therefore, this is effective in enhancement of maintenance of the effective blood concentration, i.e., prolongation of the drug efficacy, and as a result the frequency of administration (frequency of the application per unit hour) can be reduced and the burden imposed on a patient is lighten favorably.

Such a thermally plasticizing resin is preferably, for example, in a state of crystals at usual temperature and has the softening point of 50-250° C., specifically adhesiveness-giving resins including rosin or its derivative, terpene resin, terpene-phenol resin, petroleum resin, alkyl-phenol resin, xylene resin, and the like. These resins, one or more species, may be blended in an amount of 50% by weight or less, preferably in the range of 5-40% by weight.

The thickness of the plaster layer having the above components is desirably in 20-200 μm, preferably 20-100 μm so as to endure adhesion to the skin surface over a long period of time.

The percutaneous absorption-type pharmaceutical preparation of the invention may be prepared according to a conventional way. For example, an adhesive and a drug of which the solubility to the adhesive component is over saturation are dissolved in a proper solvent, and the resulting solution is applied to one side of a support, dried, and the excess drug is recrystallized out. Thus, the drug in a crystal state is dispersed homogeneously in the plaster to yield a pharmaceutical preparation.

The plane shape of the percutaneous absorption-type pharmaceutical preparation of the invention is not particularly limited, and may be in a square, a rectangle, a circle, an ellipse, and the like.

The adhesion size and frequency of change (dose) of the percutaneous absorption-type pharmaceutical preparation is variable depending on the kind of drug, age of the patient, body weight, condition, etc., and may be determined according to the amount of drug for the unit area of the preparation and the guideline for administration of each drug.

EXAMPLES

Hereinafter, the present invention will be explained in detail by the following examples and experiments, which are not intended as a limitation thereof. In the following examples, "part(s)" and "%" means part(s) by weight and % by weight, respectively.

Example 1

Under an inert gas atmosphere, 50 parts of 2-ethylhexyl acrylate, 25 parts of 2-methoxyethyl acrylate, and 25 parts of vinyl acetate were polymerized in ethyl acetate to prepare an acryl-type adhesive solution. To this solution was added tulobuterol so that its content in the plaster layer was 20%, and the mixture was stirred well and applied to a mold-releasing liner so that the thickness after drying was 40 µm, and dried to form a plaster layer.

Next, a polyester urethane-type adhesive (Tg 83° C.; Vylon UR-1400, Toyobo Co.) was applied onto a polyester film (6 µm in thickness) with a gravure coater so that the dry amount was 5 g/m$^2$, and a polyester nonwoven fabric (20 g/m$^2$) laminated thereon under heating and pressure to give a support; then, the plaster layer was put on the polyester film side and kept at 25° C. for 1 week foraging to give a percutaneous absorption-type pharmaceutical preparation of the invention. Polyisocyanate compound (Coronate HL, Nippon Polyurethane Co.) as a crosslinking agent was blended to the adhesive in a rate of 20% for 80% of major solution.

Example 2

In hexane was dissolved 35 part of high molecular weight polyisobutyrene (viscosity average molecular weight 990,000; VISTANEX MML-80, Exxon Chemical Co.), 45 parts of low molecular weight polyisobutyrene (viscosity average molecular weight 60,000; HIMOL 6H, Shin-Nippon Oil Chemical Co.), and 20 parts of alicyclic petroleum resin (softening point 100° C.; Alcon P-100, Arakawa Chemical Co.) to give a polyisobutyrene-type adhesive solution (solid concentration 25%). To this solution was added tulobuterol so that its content in the plaster layer was 10%, and the mixture was stirred well and applied to a mold-releasing liner so that the thickness after drying was 40 µm, and dried to form a plaster layer.

Next, a polyester-type adhesive Vylon GK64CS (Tg 79° C.; Toyobo Co.) was applied onto a polyester film (6 µm in thickness) with a gravure coater so that the dry amount was 5 g/m$^2$, and a polyester nonwoven fabric (20 g/m$^2$) laminated thereon under heating and pressure to give a support; then, the plaster layer was put on the polyester film side and kept at 25° C. for 1 week for aging to give a percutaneous absorption-type pharmaceutical preparation of the invention. Polyisocyanate compound (Coronate HL, Nippon Polyurethane Co.) as a crosslinking agent was blended to the adhesive in a rate of 20% for 80% of major solution.

Example 3

In hexane was dissolved 50 part of high molecular weight polyisobutyrene (viscosity average molecular weight 990,000; VISTANEX MML-80, Exxon Chemical Co.), 40 parts of low molecular weight polyisobutyrene (viscosity average molecular weight 60,000; HIMOL 6H, Shin-Nippon Oil Chemical Co.), and 10 parts of alicyclic petroleum resin (softening point 100° C.; Alcon P-100, Arakawa Chemical Co.) to give a polyisobutyrene-type adhesive solution (solid concentration 25%). To this solution was added tulobuterol so that its content in the plaster layer was 10%, and the mixture was stirred well and applied to a mold-releasing liner so that the thickness after drying was 40 µm, and dried to form a plaster layer.

The support was treated in the same manner as in Example 1, except that Vylon UR-8200 (Tg 73° C., Toyobo Co.) was used in place of the polyester urethane adhesive, and the above plaster layer was put thereon to give a percutaneous absorption-type pharmaceutical preparation.

Example 4

In hexane was dissolved 45 part of high molecular weight polyisobutyrene (viscosity average molecular weight 990,000; VISTANEX MML-80, Exxon Chemical Co.), 40 parts of low molecular weight polyisobutyrene (viscosity average molecular weight 60,000; HIMOL 6H, Shin-Nippon Oil Chemical Co.), and 15 parts of alicyclic petroleum resin (softening point 100° C.; Alcon P-100, Arakawa Chemical Co.) to give a polyisobutyrene-type adhesive solution (solid concentration 25%). To this solution was added tulobuterol so that its content in the plaster layer was 10%, and the mixture was stirred well and applied to a mold-releasing liner so that the thickness after drying was 40 µm, and dried to form a plaster layer.

The support was treated in the same manner as in Example 2, except that Vylon 20SS (Tg 67° C., Toyobo Co.) was used in place of the polyester-type adhesive, and the above plaster layer was put thereon to give a percutaneous absorption-type pharmaceutical preparation.

Example 5

In hexane was dissolved 20 part of high molecular weight polyisobutyrene (viscosity average molecular weight 990,000; VISTANEX MML-80, Exxon Chemical Co.), 50 parts of low molecular weight polyisobutyrene (viscosity average molecular weight 60,000; HIMOL 6H, Shin-Nippon Oil Chemical Co.), and 30 parts of alicyclic petroleum resin (softening point 100° C.; Alcon P-100, Arakawa Chemical Co.) to give a polyisobutyrene-type adhesive solution (solid concentration 25%). To this solution was added tulobuterol so that its content in the plaster layer was 10%, and the mixture was stirred well and applied to a mold-releasing liner so that the thickness after drying was 40 µm, and dried to form a plaster layer.

The support was treated in the same manner as in Example 1, except that Vylon UR-1350 (Tg 46° C., Toyobo Co.) was used in place of the polyester urethane adhesive, and the above plaster layer was put thereon to give a percutaneous absorption-type pharmaceutical preparation.

Comparative Example 1

In the same manner as in Example 1, a percutaneous absorption-type pharmaceutical preparation was prepared, except that Vylon 63SS (Tg 7° C., Toyobo Co.) was used in place of the polyester urethane adhesive.

Comparative Example 2

In the same manner as in Example 2, a percutaneous absorption-type pharmaceutical preparation was prepared, except that Vylon BX1OSS (Tg 18° C., Toyobo Co.) was used in place of the polyester-type adhesive.

Experiment 1

The percutaneous absorption-type pharmaceutical preparations prepared in Examples 1 to 5 and Comparative Examples 1 and 2, and the respective preparations stored at 40° C. for 3 months were examined for stability of the laminate strength with a lapse of time.
<Method for Determining the Laminate Strength>
Each sample was cut into beltlike pieces of 12 mm in width, of which the laminate portion (between the nonwoven fabric and the polyester film) was peeled off by several mm from the tip in advance. Cellophane tapes were pasted on the surface of the plaster and nonwoven fabric, respectively. At that time, an end of cellophane tape on the peeled side was lengthen by 1-2 cm, which was folded back to make a holding hinge; this hinge was intended to put into a zipper in a tension test machine (INSTRON Type RTA-100, Orientec Co.). This was peeled off in the direction of 180° at a rate of 10 mm/min to determine the laminate strength.

The preparations of Examples 1 to 5 showed stable characteristics from start, and no change of the laminate strength was observed with a lapse of time. Contrarily, in the preparations of Comparative Examples 1 and 2, decrease of the laminate strength was recognized with a lapse of time, possibly due to absorption of the drug to the adhesive.

Experiment 2

The percutaneous absorption-type pharmaceutical preparations prepared in Examples 1 to 5 and Comparative Examples 1 and 2, and the respective preparations stored at 40° C. for 3 months were examined for stability of the drug content in the plaster layer with a lapse of time. The drug content was calculated as a rate (%) for the amount indicated in the pharmaceutical preparation. In all of the examples, decrease of the drug content caused by emission of the drug from the preparation was recognized with a lapse of time. However, it was recognized that the drug content in Examples 1 to 5 was more stable than in Comparative Examples 1 and 2. In the preparations of Comparative Examples 1 and 2, most of the released drug was adsorbed onto the adhesive, and as a result it was recognized that the drug content in the plaster layer was sharply decreased.

This application is based on Japanese patent application JP 2005-256277, filed on Sep. 5, 2005, the entire content of which is hereby incorporated by reference, the same as if set forth at length.

What is claimed is:

1. A percutaneous absorption-type pharmaceutical preparation, which comprises: a support comprising a plastic film and a nonwoven fabric; and a plaster layer containing tulobuterol, wherein the plastic film and the nonwoven fabric are laminated with an adhesive having a glass transition temperature of 40° C.-90° C., and the plaster layer is laminated on opposite side of the plastic film surface that the nonwoven fabric is laminated with.

2. The percutaneous absorption-type pharmaceutical preparation as claimed in claim 1, wherein the adhesive is one selected from the group consisting of polyester resin, polyester urethane resin, polyvinyl acetate resin, ethylene-vinyl acetate resin, polyacrylate resin, and vinyl chloride-vinyl acetate copolymer resin.

3. The percutaneous absorption-type pharmaceutical preparation as claimed in claim 1, wherein the plastic film and the nonwoven fabric both are made from polyester.

4. The percutaneous absorption-type pharmaceutical preparation as claimed in claim 1, wherein the plaster layer contains the sublimation drug in an amount of 1-40% by weight.

* * * * *